United States Patent [19]
Spitzer et al.

[11] 4,152,416
[45] May 1, 1979

[54] AEROSOL ANTIPERSPIRANT COMPOSITIONS DELIVERING ASTRINGENT SALT WITH LOW MISTINESS AND DUSTINESS

[76] Inventors: Joseph G. Spitzer, 44 Coconut Row, Palm Beach, Fla. 33480; Marvin Small, 2 Fifth Ave., New York, N.Y. 10003; Lloyd I. Osipow, 1100 Park Ave., New York, N.Y. 10016; Dorothea C. Marra, 107 Fernwood Rd., Summit, N.J. 07901

[21] Appl. No.: 724,426

[22] Filed: Sep. 17, 1976

[51] Int. Cl.² .................. A61K 7/32; A61K 7/34; A61K 7/38; A61K 9/14
[52] U.S. Cl. ......................... 424/46; 424/45; 424/47; 424/65; 424/66; 424/67; 424/68
[58] Field of Search ............. 424/65, 66, 67, 68, 424/45, 46, 47

[56] References Cited

U.S. PATENT DOCUMENTS

| | | | |
|---|---|---|---|
| 3,725,540 | 4/1973 | Wahl | 424/65 X |
| 3,903,258 | 9/1975 | Siegal | 424/47 X |
| 3,929,986 | 12/1975 | Bouillon | 424/68 X |
| 3,953,450 | 4/1976 | Bouillon | 424/68 X |
| 3,956,352 | 5/1976 | Bouillon | 424/68 X |
| 3,963,833 | 6/1976 | DeSalva | 424/68 |
| 3,968,203 | 7/1976 | Spitzer | 424/47 |
| 3,974,270 | 8/1976 | Kenkare | 424/66 |
| 4,053,581 | 10/1977 | Pader | 424/68 |
| 4,065,564 | 12/1977 | Miles | 424/68 |

FOREIGN PATENT DOCUMENTS

| | | | |
|---|---|---|---|
| 2453139 | 5/1975 | Fed. Rep. of Germany | 424/65 |
| 2510364 | 9/1975 | Fed. Rep. of Germany | 424/65 |
| 1485373 | 9/1977 | United Kingdom. | |
| 1501862 | 2/1978 | United Kingdom | 424/65 |

OTHER PUBLICATIONS

Sagarin, Cos, Sci. & Tech., Intersci., N.Y., 1957, pp. 717-739.

Primary Examiner—Anna P. Fagelson

[57] ABSTRACT

Aerosol antiperspirant compositions are provided, capable of dispensing active astringent salt from aerosol containers with low mistiness and dustiness, comprising, in combination, an astringent salt in an amount within the range from about 3 to about 30%; a hydrocarbon or halocarbon propellant; a synthetic polymer gum having a viscosity within the range from about 500,000 to about 100 million centistokes at 25° C. in an amount within the range from about 0.05 to about 5% by weight of the composition; and optionally, an aliphatic, cycloaliphatic, or aromatic carboxylic acid having from about nine to about fifty carbon atoms, comprising all or part of a nonvolatile miscible organic liquid or oil in an amount within the range from about 0.1 to about 30% by weight of the composition.

26 Claims, No Drawings

AEROSOL ANTIPERSPIRANT COMPOSITIONS DELIVERING ASTRINGENT SALT WITH LOW MISTINESS AND DUSTINESS

Aerosol sprays are now widely used, particularly in the cosmetic, topical pharmaceutical and detergent fields, for delivery of an additive such as a cosmetic, pharmaceutical, or cleaning composition to a substrate such as the skin or other surface to be treated. Aerosol compositions are widely used as antiperspirants to direct the antiperspirant to the skin in the form of a finely divided spray.

The delivery of antiperspirants to the skin in a fine spray poses a difficult aerosol packaging problem. Aerosol antiperspirant compositions based on anhydrous propellant systems normally include antiperspirant, filler and other solid particles dispersed in a liquid vehicle, and the solid particles readily clog small valve orifices. On the other hand, if the orifices are large enough to avoid clogging, a coarse liquid spray with large droplets is formed, and there may be excessive drip at the nozzle. The material can even be squirted out in the form of a liquid stream, which rapidly runs off the surface on which it is deposited.

Much effort has accordingly been directed to the design of valves and valve delivery ports, nozzles or orifices which are capable of delivering finely-divided sprays, of which U.S. Pat. Nos. 3,083,917 and 3,083,918 patented Apr. 2, 1963, to Abplanalp et al., and U.S. Pat. No. 3,544,258, dated Dec. 1, 1970, to Presant et al., are exemplary. The latter patent describes a type of valve which is now rather common, giving a finely atomized spray, and having a vapor tap, which includes a mixing chamber provided with separate openings for the vapor phase and the liquid phase to be dispensed into the chamber, in combination with a valve actuator or button of the mechanical breakup type. Such valves provide a soft spray with a swirling motion. Another design of valves of this type is described in U.S. Pat. No. 2,767,023. Valves with vapor taps are generally used where the spray is to be applied directly to the skin, since the spray is less cold.

Presant et al. in U.S. Pat. No. 3,544,258, referred to above, discloses a vapor tap having a stem orifice 0.018 inch in diameter, a vapor tap 0.023 inch in diameter with a capillary dip tube 0.050 inch in diameter. The button orifice diameter was 0.016 inch. The composition dispensed is an aluminum antiperspirant comprising aluminum chlorhydroxide, water, alcohol and dimethyl ether. The aluminum chlorhydroxide is in solution in the water, and there is therefore only one liquid phase. The dimensions of the orifices provided for this composition are too small to avoid clogging, in dispensing an aluminum antiperspirant composition containing dispersed astringent salt particles.

The vapor tap type of valve is effective in providing fine sprays. However, it requires a high proportion of propellant, relative to the amount of active ingredients dispensed per unit time. A vapor tap requires a large amount of propellant gas, because the tap introduces more propellant gas into each squirt of liquid. Such valves therefore require aerosol compositions having a rather high proportion of propellant. This however poses other difficulties. The fine sprays that are dispensed give rise to stable aerosols of the finely divided liquid particles, referred to as mistiness, and the high proportion of propellant produces a fine dust of the suspended solids, which settles only slowly, and is referred to as dustiness. The high proportion of propellant also leads to difficulty in adhering the astringent salt to the skin.

Another problem with such valves is that since they deliver a liquid propellant-aerosol composition mixture, and have valve passages in which a residue of liquid remains following the squirt, evaporation of the liquid in the valve passages after the squirt may lead to deposition of solid materials upon evaporation of liquids, and valve clogging. This problem has given rise to a number of expedients, to prevent the deposition of solid materials in a form which can result in clogging.

Consequently, it has long been the practice to employ large amounts of liquefied propellant, say 50% by weight or more, to obtain fine droplets of liquid sprays or fine powder sprays, and a rather small solids content, certainly less than 10%, and normally less than 5%. The fine sprays result from the violent boiling of the liquefied propellant after it has left the container. A case in point is exemplified by the dispersion-type aerosol antiperspirants, which contain 5% or less of astringent powder dispersed in liquefied propellant. It has not been possible to use substantially higher concentrations of astringents without encountering severe clogging problems, increased dustiness, and poor adherence to the skin.

In accordance with the invention, aerosol antiperspirant compositions are provided that are capable of being dispensed from aerosol containers with low mistiness and dustiness, comprising, in combination, an astringent salt in an amount within the range from about 3 to about 30%; a liquid phase comprising a propellant in an amount within the range from about 15% to about 95%; a synthetic polymer gum having a viscosity within the range from about 500,000 to about 100 million centistokes at 25° C. in an amount within the range from about 0.05 to about 5% by weight of the composition to increase the viscosity of the liquid phase and inhibit mistiness and dustiness; and optionally, a nonvolatile miscible organic liquid in an amount within the range from about 0.1 to about 30% by weight of the composition, of which organic liquid all or part optionally comprises an aliphatic, cycloaliphatic or aromatic carboxylic acid having from about nine to about fifty carbon atoms that enhances adhesion of the antiperspirant salt to the skin.

Further in accordance with the invention, aerosol antiperspirant compositions are provided that are highly concentrated with respect to the active antiperspirant, and capable of being dispensed from aerosol containers of the foam type at a low delivery rate in a propellant gas:liquid ratio in excess of 10:1, comprising, in combination, a liquid phase comprising a nonvolatile miscible organic liquid in an amount within the range from about 0.1 to about 30% by weight of the composition, and an antiperspirant salt in an amount within the range from about 3 to about 30% by weight of the composition; a propellant having a low molecular weight and a vapor pressure at 21° C. of at least 2.4 atmospheres absolute, and present in an amount of at least 0.15 mole per atmosphere absolute pressure in the container at 21° C. per 100 g of composition, to generate an expelled gas:liquid ratio in excess of 10:1, and a synthetic polymer gum having a viscosity within the range from about 500,000 to about 100 million centistokes at 25° C. in an amount within the range from about 0.05 to about 5% by weight of the composition, to increase the viscosity of the liquid phase and inhibit formation of stable aerosol dispersions in air of the liquid and solid phases when the composition is expelled from an aerosol container and thus reduce mistiness and dustiness.

The polymer gums are either soft or rubbery solids, or highly viscous materials, flowable under stress, but too slowly flowable to be properly described as oils or liquids. Any synthetic polymer having a viscosity within this range can be used provided it is soluble in the liquid phase (including the propellant and any nonvolatile liquid). Silicone gums, and especially silicone polymers of the dimethyl polysiloxane type, and acrylic and hydrocarbon polymers, are available within this range and are preferred.

The term "gum" is used to refer to a material that has a viscosity within the range from about 500,000 to about 100 million centistokes at 25° C., because it is normally slowly flowable, as opposed to a rigid solid, which is not flowable, or a liquid, which is too flowable.

An approximate empirical relationship between the viscosity of linear silicone gum polymers and their average molecular weights is given in Kirk-Othmer, *Encyclopedia of Chemical Technology*, Interscience Publishers 18 226 (Second Edition, 1969):

$$\log (\text{viscosity in centistokes at 25° C.}) = (1.00 + 0.0123 M_n 1/2)$$

where $M_n$ is average molecular weight.

This relationship suggests that useful linear silicone gums fall within the molecular weight range of about 140,000 to 350,000. However, branched-chain silicone gums are also useful, and have higher molecular weights at the same viscosity, depending on the degree of branching. Highly branched silicone gums have molecular weights extending to about 2 million.

Particularly useful are silicone gums of the dimethyl polysiloxane type. These may have other groups attached, such as phenyl, vinyl, cyano, or acrylic, but the methyl groups should be in a major proportion.

Silicone polymers having a viscosity below about 100,000 centistokes (molecular weight below about 100,000) at 25° C. are not gums; they are oils, and are ineffective in reducing a tendency towards stable aerosol formation, i.e. mistiness and dustiness.

Acrylic polymer gums which can be used include octyl methacrylate, octadecyl methacrylate, butyl acrylate, isobutyl acrylate, copolymers of butyl acrylate and isobutyl acrylate, copolymers of octyl methacrylates, heptyl methacrylates and nonyl methacrylates; copolymers of butyl methacrylate and butyl acrylate; and copolymers of butyl methacrylate and isobutyl acrylate; and copolymers of any one or more of these with acrylonitrile, isoprene, isobutylene or butadiene. These gums can have a molecular weight within the range from about 30,000 to about 2,000,000, but the molecular weight is not critical.

Hydrocarbon polymer gums that can be used include polyisobutylene, polyisoprene, isobutylene-isoprene copolymers, and chloroisobutylene-isoprene copolymers, and polybutadiene. Hydrocarbon polymer gums can have a molecular weight within the range from about 30,000 to about 2,000,000, but the molecular weight is not critical.

The amount of polymer gum is within the range from about 0.05 to about 5% and preferably from about 0.1 to about 2%, by weight of the composition. The higher the molecular weight or viscosity of the polymer gum, the less of it is required to reduce mistiness.

It is important that the polymer gum be soluble in the liquid phase of the composition. It is advantageous but not essential that the polymer be soluble in the nonvolatile oil component of the composition. If the polymer is not soluble, and is of a rubbery or soft solid consistency, residues in the valve or actuator button may have a tendency to cause clogging. This can be avoided by adding a lubricant. Any conventional lubricant can be used. Silicone oils are useful lubricants, and so also may be the nonvolatile organic liquid.

The propellant propels the aerosol composition from the aerosol container and sprays it towards the skin target. Any liquefied propellant having a boiling point within the range from about −45° C. to about +5° C. can be used, including the hydrocarbons and the fluorocarbons.

When the composition containing liquefied propellant is expelled as a spray of liquid droplets from the container, and the pressure is reduced to atmospheric, the liquefied propellant in the spray begins to volatilize. At normal atmospheric temperature and pressure, the liquefied propellant may not have evaporated completely by the time the spray reaches the skin. This may impart a cold feel to the spray after it lands on the skin. A gaseous propellant does not give this effect, since it is a gas and escapes before the spray reaches the skin. The spray from such a composition has a dry feel.

To increase dry feel, it is possible to use liquefied propellants having a low boiling point, below about 5° C. and preferably below about −10° C. Propellants having a boiling point below about −45° C. are not practical to use, because they require very high pressures within the aerosol container, as a result of which the amount that can be incorporated as limited, due to the limited pressure resistance capability of conventional aerosol containers.

Propellants which meet the requirements and can be used include the chemically inert hydrocarbons such as propane, n-butane, isobutane and cyclopropane as well as halogenated hydrocarbons such as dichlorodifluoromethane (Propellant 12), and 1,1-dichloro-1,1,2,2-tetrafluoroethane (Propellant 114), 1-chloro-1,1-difluoro-2,2-trifluoroethane (Propellant 115), 1-chloro-1,1-difluoroethylene (Propellant 142B), 1,1-difluoroethane (Propellant 152A), and monochlorodifluoromethane.

Liquids which boil at above 5° C. can be used as solvents, rather than as propellants. Such liquids include trichlorotrifluoroethane, dichloromonofluoromethane, methylene chloride, and trichlorofluoromethane (Propellant 11).

In these compositions, propellants having a vapor pressure at 21° C. of at least 2.4 atmospheres absolute in an amount of at least 0.15 mole per atmosphere absolute pressure at 21° C. per 100 g of composition are capable of generating under pressure within containers of the foam type a sufficient volume of gas to expel all of the liquid composition contents in a gas:liquid volume ratio from about 10:1 to about 40:1 where the volume of gas expelled is calculated at the pressure inside the container. Such propellants are therefore preferred, for use in such containers.

Exemplary hydrocarbon propellants within this more limited class include n-butane, isobutane, propane, and cyclopropane. Isobutane is particularly preferred, because of its vapor pressure. Propane has a lower molecular weight than isobutane, but a substantially higher vapor pressure, and provides only half the volume of propellant gas at the internal pressure of the container as does isobutane. Cyclopropane provides a volume of gas intermediate between propane and isobutane. It is generally preferred that the propellant mixture in the compositions of the invention contain at least 20% by weight of isobutane and that the proportion of isobutane by weight of the entire composition should be at least 15%. Mixtures of isobutane with propane, cyclopropane and butane can be used. Mixtures of isobutane and propane are preferred.

Halocarbon propellants which can be used alone or in admixture with hydrocarbon propellants include dichlorodifluoromethane, 1,2-dichlorotetrafluoroethane, chlorodifluoromethane, 1,1-difluoroethane, and 1-chloro-1,1-difluoroethane.

Halocarbons that are not propellants, such as trichlorofluoromethane, dichlorofluoromethane, methylene chloride and 1,1,1-trichloromethane, also can be employed to reduce the flammability of a hydrocarbon propellant.

Combinations of one or more of these propellants and non-propellants with iobutane are especially preferred. Selected hydrocarbons and halocarbons can be used in admixture, to give exactly the vapor pressure and gas volume desired for a particular aerosol formulation.

Dispersion-type aerosol antiperspirant compositions in general are composed of an astringent salt in combination with a nonvolatile miscible orgnic liquid such as isopropyl myristate to improve adherence of the astringent salt to the skin. This type of formulation is described in many patents, including for example, U.S. Pat. No. 3,968,203, patented July 6, 1976 to Spitzer et al., U.S. Pat. No. 3,725,540, patented Apr. 3, 1973 to Wahl, U.S. Pat. No. 3,903,258 patented Sept. 2, 1975 to Siegal, and U.S. Pat. No. 3,959,459, patented May 25, 1976 to Curry. These liquids are frequently referred to as nonvolatile oils, as liquid carriers, and as emollients, and the function of the nonvolatile liquid is to adhere the astringent salt to the skin.

The term "nonvolatile" means that the liquid will not volatilize during the time the composition is on the skin and before it is adsorbed. This usually requires only a few minutes. Thus, the term "nonvolatile" does not exclude materials that are slowly volatile and require a long time to evaporate fully, such as the volatile silicones. These are generally poly dimethyl siloxanes of low viscosity, about 2 or 3 centistokes at 25° C.

The amount of nonvolatile liquid that is employed is selected on the basis of the amount of astringent salt present. The upper limit on the amount used is that which leads to excessive oiliness in the feel of the composition after deposition on the skin.

In general, the amount of nonvolatile liquid should be at least 1% but should not exceed about 200% by weight of the astringent salt.

Suitable examples include fatty acid esters of polyalkylene glycols wherein the fatty acid contains from about two to about twenty carbon atoms, and from about two to about two hundred alkylene glycol units per fatty acid molecule; fatty acid esters of aliphatic alcohols where the esters contain from about twelve to about twenty-six carbon atoms, such as ethyl laurate, isopropyl myristate, isopropyl palmitate, isopropyl behenate, decyl acetate, behenyl butyrate, hexadecyl acetate, decyl decanoate, methyl oleate, lauryl laurate, and oleyl acetate; esters containing multiple ester groups such as those disclosed in British patent specification No. 1,353,914, that is multiple ester organic compounds of from about twelve to about sixteen carbon atoms having a ratio of ester groups to carbon atoms of from 0.125 to 0.214 and having a solubility in water of 0.0005% to 0.1% at 30° C., examples being di-n-octyl-n-decyl phthalate, di-n-octyl phthalate, di-n-hexyl phthalate, di-n-butyl phthalate, diethyl sebacate, diisopropyl adipate, and ethyl ethoxycarbonyl phthalate

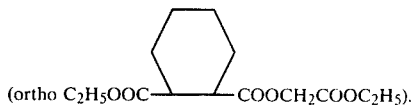

(ortho C$_2$H$_5$OOC— —COOCH$_2$COOC$_2$H$_5$).

Liquids more hydrophilic than these esters include polyethylene glycol monolaurate and Fluid AP, a product of the Union Carbide Company.

Among these various liquid carboxylic acid esters, those having from about twelve to about twenty-six carbon atoms are preferred. As described above, they can be either aliphatic or aromatic and can contain either one or more ester groups. Especially preferred are the esters, e.g. di-n-butyl phthalate, diethyl sebacate, diisopropyl adipate and ethyl ethoxycarbonyl phthalate and Fluid AP.

While the function of the nonvolatile liquid is to adhere the astringent salt to the skin, many of these oils have an insufficient bonding capacity to be more than moderately effective in this respect.

Accordingly, as an adherence-promoting agent more effective for this purpose, there can optionally be included in compositions of the invention, as part or all of the nonvolatile liquid component, a carboxylic acid having from about nine to about fifty carbon atoms and selected from aliphatic, cycloaliphatic and aromatic carboxylic acids. Both straight and branched-chain saturated and unsaturated aliphatic acids are satisfactory, as well as cycloaliphatic acids and aromatic acids, in which the aromatic ring is a single benzene nucleus or a condensed polybenzene nucleus such as naphthalene, anthracene or phenanthrene. The acid can have more than one carboxylic acid group, and it can also contain other groups, such as hydroxyl, amido, ether and carboxylic acid ester groups.

Thus, the class of carboxylic acids which can be employed as adherence-promoting agents in the compositions of the invention include carboxylic acids having from about nine to about fifty carbon atoms, from one to four carboxylic acid groups, and, optionally, from one to four hydroxyl and/or ester or ether or amido groups.

The preferred carboxylic acids are the aliphatic carboxylic acids having from about nine to about twenty-two carbon atoms. Those particularly preferred are the saturated carboxylic acids that have from about fourteen to about twenty-two carbon atoms in straight chain.

Exemplary carboxylic acids include lauric acid, palmitic acid, myristic acid, stearic acid, behenic acid, margaric acid, oleic acid, linoleic acid, linolenic acid, ricinoleic acid, isostearic acid, the fatty acid mixtures derived from natural fats and oils such as tung oil fatty acids, safflower oil fatty acids, coconut oil fatty acids, corn oil fatty acids, cottonseed oil fatty acids, fish oil fatty acids, whale oil fatty acids, sunflower oil fatty acids, sesame seed oily fatty acids, linseed oil fatty acids, castor oil fatty acids, and tallow fatty acids.

Examples of cycloaliphatic acids include abietic acid, chaulmoogra oil fatty acids, naphthenic acid, the 36 carbon atoms dimer acid, and the 54 carbon trimer acid. Aromatic acids include acetyl salicyclic acid, dodecylsalicylic acid, butoxybenzoic acid, and oxtoxybenzoic acid.

Examples of carboxylic acids containing other groups include lauroyl sarcosine, oleoyl sarcosine, stearoyl sarcosine, oleoyl lactylate and stearoyl lactylate. The sarcosines contain an amidomethyl group. The lactylates are prepared by esterifying one mole of fatty acid with two or more moles of lactic acid, and thus contain two or more ester groups.

The amount of carboxylic acid that is employed is selected for the degree of adhesion desired, and according to the specific carboxylic acid, or mixture of carboxylic acids, that is employed, the amount of astringent salt present, and the particle size of the astringent salt.

In general, less carboxylic acid is required if the carboxylic acid is saturated, straight-chain fatty acid, than if it is a branched-chain or unsaturated fatty acid. Also, less is required if it contains fourteen or more carbon atoms. Thus, in the case of palmitic acid and stearic acid, 1 or 2% of carboxylic acid based on the weight of the astringent salt may be equivalent in effect to from about 10 to about 15% of isostearic acid or oleic acid by weight of the atringent salt.

At high levels of carboxylic acid, adhesion of the astringent salt to the skin may be so effective that the salt is difficult to remove by washing. If the carboxylic acid is a liquid, the use of a large amount may lead to excessive oiliness in the feel of the composition after deposition on the skin. If the carboxylic acid is a solid, large amounts may result in crystallization. and possible clogging of the valve. The carboxylic acid may be used in combination.

The following Table illustrates the amounts of carboxylic acids that are preferably employed in the composition:

|  | Astringent Salt Basis Weight % | Composition Basis Weight % |
|---|---|---|
| Nine to fifty carbon atom carboxylic acid | 1–100 | 0.1–30 |
| Nine to twenty-two carbon atom aliphatic carboxylic acid | 1–100 | 0.1–30 |
| Nine to twenty-two carbon atom unsaturated or branched-chain aliphatic carboxylic acid | 10–100 | 1–30 |
| Fourteen to twenty-two carbon atom saturated straight-chain aliphatic carboxylic acid | 1–5 | 0.1–1.5 |

As the astringent salt, any antiperspirant aluminum or zirconium salt can be employed in the antiperspirant compositions of the invention.

Suitable antiperspirant aluminum and/or zirconium salts are any of those well known in the art, whether soluble or insoluble in the antiperspirant compositions of the invention. Generally, these are acidic inorganic salts of aluminum and zirconium. Examples of aluminum and zirconium salts are aluminum chlorhydroxide, aluminum chloride, aluminum sulfate, aluminum oxychloride, aluminum oxysulfate, zirconyl chloride, zirconyl hydroxychloride, and zirconium oxychloride.

Many inorganic-organic mixtures and complexes are also known astringent salts, such as zirconium salt/amine/and amino acid complexes, Siegel U.S. Pat. No. 3,407,254; zirconium salt/aluminum chlorhydroxide/glycol complexes, Jones et al U.S. Pat. No. 3,405,153; aluminum chlorhydroxide/glycol complexes, Jones et al U.S. Pat. No. 3,402,932; aluminum chlorhydroxide/zirconyl hydroxychloride complexes; and aluminum hydroxide/zirconyl hydroxychloride/amino acid complexes. Also useful are the aluminum and zirconium salts complexed with polyols such as propylene glycol.

As the antiperspirant aluminum and/or zirconium salt, in accordance with the invention, aluminum chlorhydroxide and zirconium chlorhydroxide, and mixtures of aluminum chlorhydroxide and zirconium chlorhydroxide, with or without aluminum chloride or sulfate, are preferred. Aluminum chloride and sulfate can also be used, but these are less preferred.

In order to prevent caking or settling out of the astringent salt in the compositions of the invention, so that it cannot be dispensed from the aerosol container, a bulking agent can be incorporated. This is a finely divided particulate material, inert and insoluble in the liquids present, having a particle size below 10 microns in diameter, and includes colloidal silica and hydrophobic clays.

The colloidal silica is preferably a pyrogenic silica, but other types of silica particles of colloidal sizes may be employed. The colloidal silica will normally be of particle size less than 100 m$\mu$, preferably averaging less than 50 m$\mu$ in diameter. Among the more preferred pyrogenic silicas the diameters will be in the 2 to 20 m$\mu$ range. The ultimate particle size (diameter) of a preferred pyrogenic silica, that sold by Cabot Corporation, Boston, Massachusettes, as Cab-O-Sil M-5 (Cab-O-Sil is a trademark), is about 11 m$\mu$, while the corresponding H-5grade has a diameter of about 7 m$\mu$. The surface areas of the pyrogenic colloidal silicas and other colloidal silicas having an average particle size less than one micron are exceptionally great, often resulting from about 50 to 500 square meters per gram, leading to desirable thickening, suspending and covering properties. The particles are also of generally spherical shape.

Examples of hydrophobic treated clays that swell in organic solvents include hydrophobic bentonite, e.g. Bentone (Registered Trade Mark) 38, and other Bentones, which are bentonite treated with a hydrophobic cationic material such a ditallowalkyldimethylammonium chloride In addition to the propellant, an organic solvent can be added. The solvent reduces the vapor pressure and the viscosity of the composition as well as the oiliness of the deposit on the skin. In the case of nonflammable solvents, it also reduces the flammability of the spray. Suitable solvents for this purpose are pentane, hexane, trichlorotrifluoroethylene, trichlorofluoromethane, dichlorofluoromethane, and methylene chloride. Many hydrocarbon and halocarbon liquefied propellants also serve the same purpose, however, if they remain in the deposit on the skin.

In addition to the above-mentioned ingredients, there can be employed the customary adjuncts of aerosol antiperspirant compositions, such as perfumes, bactericides, fungicides, emollients, and other skin-treating materials.

The aerosol compositions in accordance with the invention can be defined by the following general formulation ranges:

|  | Parts Overall By Weight | Preferred Parts By Weight |
|---|---|---|
| Antiperspirant Salt | 3 to 30 | 5 to 15 |
| Bulking Agent | 0.1 to 5 | 0.2 to 2 |
| Nonvolatile liquid | 0 to 30 | 0.1 to 20 |
| Carboxylic acid[1] | 0 to 30 | 0.1 to 15 |
| Polymer gum | 0.05 to 5 | 0.1 to 2 |
| Propellant | 15 to 95 | 30 to 95 |
| Other volatile solvents | 0 to 79 | 0 to 30 |

[1]The carboxylic acid is part or all of the nonvolatile liquid.

The following Examples in the opinion of the inventors represent preferred embodiments of their invention. In the Examples, in addition to the formulations, the dimensions of the important components of the foam-type aerosol container in which such a composition is best used are also given.

EXAMPLE 1

An aerosol antiperspirant composition was prepared having the following formulation:

|  | Parts by Weight |
|---|---|
| Aluminum chlorhydroxide | 10.3 |
| Oleic acid | 2.5 |
| Isopropyl myristate | 7.8 |
| Silicone gum, 2 million centistokes at 25° C. (polydimethyl siloxane) | 1.4 |
| Cab-O-Sil silica | 1.0 |
| Isobutane | 65.0 |
| Propane | 12.0 |

The colloidal silica, oleic acid, and isopropyl myristate were placed in a Waring Blendor, and mixed at high speed for five minutes. The dispersion was then mixed with the aluminum chlorhydroxide and silicone gum, and homogenized.

The composition was then filled into an aerosol container of the type shown in FIGS. 1, 1A and 2 of Ser. No. 706,857, filed July 19, 1976, having the dimensions shown below, and pressurized with the isobutanepropane mixture.

|  | Internal Diameter | |
|---|---|---|
|  | Inch | mm |
| Valve stem orifice | 0.020 | 0.51 |
| Bubbler orifice | 0.030 | 0.76 |
| Capillary dip tube | 0.040 | 1.0 |
| Actuator orifice | 0.020 | 0.51 |

In a two-second spray application, there was expelled 0.8 g of antiperspirant composition, which deposited on the skin 0.060 g of astringent salt. The composition was quite effective in inhibiting perspiration for one day.

EXAMPLE 2

An aerosol antiperspirant composition was prepared having the following formulation:

|  | Parts by Weight |
|---|---|
| Aluminum chlorhydroxide | 8.4 |
| Decyl oleate | 8.3 |
| Butyl 077[1] | 1.0 |
| Bentone 38 bentonite clay | 0.3 |
| Isobutane | 18.0 |
| Trichlorofluoromethane | 32.0 |
| Dichlorofluoromethane | 32.0 |

[1]Exxon Chemicals, isobutylene-isoprene copolymer gum, viscosity average molecular weight 425,000 (Flory)

The hydrophobic bentonite clay was combined with the decyl oleate and mixed in a Waring Blendor at high speed for five minutes, then combined with the aluminum chlorhydroxide and homogenized. The polymer gum was dissolved in the trichlorofluoromethane at 0° C. by stirring in a closed container for two hours. The dispersion was cooled and combined with the polymer solution.

The composition was then poured into an aerosol container of the type shown in FIGS. 1, 1A and 2 of Ser. No. 706,857, filed July 19, 1976. The composition was then pressurized by the addition of the isobutane, and dichlorofluoromethane.

The aerosol container has the following dimensions:

|  | Internal Diameter | |
|---|---|---|
|  | Inch | mm |
| Valve stem orifice | 0.020 | 0.51 |
| Bubbler orifice | 0.025 | 0.64 |
| Capillary dip tube | 0.040 | 1.0 |
| Actuator orifice | 0.020 | 0.51 |

A two-second application from the container expelled 1.3 g of antiperspirant composition, and deposited 0.10 g of aluminum chlorhydroxide on the skin. The composition was effective for one day in inhibiting perspiration.

EXAMPLE 3

An aerosol antiperspirant composition was prepared having the following formulation:

|  | Parts by Weight |
|---|---|
| Aluminum chlorhydroxide | 13.0 |
| Diisopropyl adipate | 5.4 |
| Isopropyl myristate | 5.4 |
| Silicone gum, 2 million centistokes at 25° C. (polydimethyl siloxane) | 2.0 |
| Cab-O-Sil-silica | 1.2 |
| Isobutane | 73.0 |

The colloidal silica was combined with the diisopropyl adipate and isostearic acid and mixed in a Waring Blendor at high speed for five minutes. The dispersion was then combined with the aluminum chlorhydroxide and silicone gum and homogenized. The composition was filled into aan aerosol container of the type shown in FIGS. 1 and 2 of Ser. No. 670,913 filed Mar. 26, 1976, having the dimensions shown below and pressurized with isobutane.

|  | Internal Diameter | |
|---|---|---|
|  | Inch | mm |
| Valve stem orifice | 0.025 | 0.64 |
| Foam chamber, height × diameter | 1.0 × 0.3 | 25 × 8 |
| Bubbler orifice | 0.040 | 1.0 |
| Capillary dip tube | 0.040 | 1.0 |
| Actuator orifice | 0.025 | 0.64 |

A two-second application of the composition expelled 1.0 g of spray, and deposited on the skin 0.065 g aluminum chlorhydroxide. This was effective to inhibit perspiration for one day.

EXAMPLE 4

An aerosol antiperspirant composition was prepared having the following formulation:

|  | Parts by Weight |
| --- | --- |
| Aluminum chlorhydroxide | 8.0 |
| Oleic acid | 3.0 |
| Ispropyl myristate | 9.6 |
| Butyl 077[1] | 1.0 |
| Bentone 38 bentonite clay | 0.4 |
| 1-chloro-1,1-difluoroethane | 70.0 |
| Chlorodifluoromethane | 8.0 |

[1] Exxon Chemicals, isobutylene-isoprene copolymer gum, viscosity average molecular weight 425,000 (Flory)

The hydrophobic bentonite clay Bentone 38 was mixed with the isopropyl myristate and oleic acid in a Waring Blendor at high speed for five minutes. The dispersion was then combined with the aluminum chlorhydroxide and homogenized.

The dispersion was then cooled to 15° C. and combined with the Butyl 077 gum and 20 parts of 1-chloro-1,1-difluoroethane at the same temperature in a closed container, and stirred for two hours to dissolve the gum.

The composition was then filled into aerosol containers of the type shown in FIGS. 1, 1A and 2 of Ser. No. 706,857 filed July 19, 1976. The composition was then pressurized by the addition of the remainder of the 1-chloro-1,1-difluoroethane and the chlordifluoromethane.

The aerosol container had the following dimensions:

|  | Internal Diameter | |
| --- | --- | --- |
|  | Inch | mm |
| Valve stem orifice | 0.020 | 0.51 |
| Bubbler orifice | 0.035 | 0.89 |
| Capillary dip tube | 0.040 | 1.0 |
| Actuator orifice | 0.025 | 0.64 |

In a two-second application of the composition there was expelled 1.1 g of composition, which deposited on the skin 0.080 g aluminum chlorhydroxide. This was effective to inhibit the development of perspiration odor for one day.

EXAMPLE 5

An aerosol antiperspirant composition was prepared having the following formulation:

|  | Parts by Weight |
| --- | --- |
| Aluminum chlorhydroxide | 9.0 |
| Trimer acid[1] | 2.0 |
| Decyl oleate | 6.1 |
| Silicone gum, 20 - 50 million centistokes at 25° C. (polydimethyl siloxane) | 0.3 |
| Silicone fluid, plasticizer, 100 centistokes at 25° C. | 1.6 |
| Cab-O-Sil silica | 1.0 |
| Propane | 13.0 |
| Isobutane | 67.0 |

[1] Emery Industries, Empol 1041, a 54 carbon, cyclic tribasic acid

The colloidal silica, trimer acid and decyl oleate were placed in a Waring Blendor and mixed at high speed for five minutes. The dispersion was then mixed with the aluminum chlorhydroxide, and the silicone gum plasticized by the silicone oil, and homogenized.

The composition was then filled into an aerosol container of the type shown in FIGS. 1 and 2 of Ser. No. 670,913 filed March 26, 1976, having the dimensions shown below, and pressurized with the isobutane-propane mixture.

|  | Internal Diameter | |
| --- | --- | --- |
|  | Inch | mm |
| Valve stem orifice | 0.025 | 0.64 |
| Foam chamber, height × diameter | 1.0 × 0.3 | 25 × 8 |
| Bubbler orifice | 0.040 | 1.0 |
| Capillary dip tube | 0.040 | 1.0 |
| Actuator orifice | 0.025 | 0.64 |

In a two-second spray application, there was expelled 1.1 g of antiperspirant composition, which deposited on the skin 0.080 g of astringent salt. The composition was quite effective in inhibiting perspiration for one day.

EXAMPLE 6

An aerosol antiperspirant composition was prepared having the following formulation:

|  | Parts by Weight |
| --- | --- |
| Aluminum chlorhydroxide | 8.0 |
| Isopropyl myristate | 12.8 |
| Silicone gum 10–20 million centistokes at 25° C. (polydimethyl siloxane) | 0.4 |
| Cab-O-Sil silica | 0.8 |
| Propane | 12.0 |
| Isobutane | 66.0 |

The silicone gum was dissolved in two parts of the isopropyl myristate by heating while stirring. The colloidal silica was added to the remainder of the isopropyl myristate and the dispersion was mixed in a Waring Blendor at high speed for five minutes, then combined with the aluminum chlorhydroxide and the gum solution, and homogenized.

The composition was then poured into an aerosol container of the type shown in FIGS. 3 and 4 of Ser. No. 706,857 filed July 19, 1976. The composition was then pressurized by the addition of the isobutane and propane.

The aerosol container had the following dimensions:

|  | Internal Diameter | |
| --- | --- | --- |
|  | Inch | mm |
| Valve stem orifice | 0.025 | 0.64 |
| Valve body housing orifice | 0.035 | 0.89 |
| Bubbler orifice | 0.030 | 0.76 |
| Dip tube | 0.15 | 3.8 |
| Actuator orifice | 0.025 | 0.64 |

A two-second application from the container expelled 0.8 g of antiperspirant composition, and delivered 0.060 g of aluminum chlorhydroxide to the skin. The composition was effective for one day to inhibit perspiration.

EXAMPLE 7

An aerosol antiperspirant composition was prepared having the following formulation:

|  | Parts By Weight |
| --- | --- |
| Aluminum chlorhydroxide | 10.0 |
| Isostearic acid | 4.5 |
| Isopropyl myristate | 5.6 |
| Silicone gum, 10-20 million centistokes at 25° C. | 0.4 |
| Silicone fluid, 500 centistokes at 25° C. | 1.5 |
| Cab-O-Sil silica | 1.0 |
| Propane | 10.0 |
| Isobutane | 67.0 |

The colloidal silica was combined with the isopropyl myristate and isostearic acid, and mixed in a Waring Blendor at high speed for 5 minutes. The silicone gum was dissolved in the silicone fluid by heating with stirring. The dispersion was then combined with the silicone solution and aluminum chlorhydroxide, and homogenized. The composition was filled into an aerosol container of the type shown in FIGS. 1 and 2 of Ser. No. 670,913 filed March 26, 1976, having the following dimensions:

|  | Internal Diameter | |
| --- | --- | --- |
|  | Inch | mm |
| Valve stem orifice | 0.025 | 0.64 |
| Foam chamber, height × diameter | 1.0 × 0.3 | 25 × 8 |
| Bubbler orifice | 0.040 | 1.0 |
| Capillary dip tube | 0.040 | 1.0 |
| Actuator orifice | 0.025 | 0.64 |

The contents of the container was then pressurized with the isobutane and propane.

A two-second application expelled 1.0 g of the composition, and delivered to the skin 0.060 g aluminum chlorhydroxide. This was effective to inhibit perspiration for one day.

EXAMPLE 8

An aerosol antiperspirant was prepared in accordance with the following formulation:

|  | Parts by Weight |
| --- | --- |
| Aluminum chlorhydroxide | 4.0 |
| Dibutyl phthalate | 4.0 |
| Isostearic acid | 1.7 |
| Bentone 38 bentonite clay | 0.3 |
| Silicone gum, 2 million centistokes at 25° C. | 2.0 |
| Isobutane | 23.0 |
| Trichlorofluoromethane | 27.0 |
| Dichlorodifluoromethane | 28.0 |

The hydrophobic bentonite clay was combined with the dibutyl phthalate and isostearic acid and mixed in a Waring Blendor at high speed for five minutes. The aluminum chlorhydroxide and silicone gum were then added, and the dispersion was homogenized.

The dispersion was packaged in a conventional container and pressurized with a mixture of isobutane, trichlorofluoromethane, and dichlorodifluoromethane. The dimensions were as follows:

|  | Internal Diameter | |
| --- | --- | --- |
|  | Inch | mm |
| Valve stem orifice | 0.025 | 0.64 |
| Body housing orifice | 0.080 | 2.0 |
| Vapor tap orifice | 0.020 | 0.51 |
| Dip tube | 0.12 | 3.1 |
| Actuator orifice | 0.020 | 0.51 |

A two-second spray expelled 2.0 g of the composition and deposited 0.065 g of aluminum chlorhydroxide on the skin. The composition was effective in inhibiting perspiration for one day.

EXAMPLE 9

An aerosol antiperspirant was prepared in accordance with the following formulation:

|  | Parts by Weight |
| --- | --- |
| Aluminum chlorhydroxide | 6.0 |
| Isopropyl myristate | 4.2 |
| Cab-O-Sil silica | 0.5 |
| Silicone gum, 10 - 20 million centistokes at 25° C. | 0.3 |
| Trichlorofluoromethane | 50.0 |
| Dichlorodifluoromethane | 39.0 |

The polymer gum was dissolved in the isopropyl myristate by heating with stirring. The silica was added and mixed in a Waring Blendor at high speed for five minutes. The aluminum chlorhydroxide was added, and the mixture was homogenized.

The composition was packaged in a container of the same dimensions as that of Example 8, and pressurized with a mixture of trichlorofluoromethane and dichlorodifluoromethane.

A two-second spray expelled 2.0 g of the composition, and deposited 0.10 g of aluminum chlorhydroxide on the skin. The composition was effective in inhibiting perspiration for one day.

EXAMPLE 10

An aerosol antiperspirant was prepared in accordance with the following formulation:

|  | Parts by Weight |
| --- | --- |
| Aluminum chlorhydroxide | 5.0 |
| Diisopropyl sebacate | 4.0 |
| Oleic acid | 1.0 |
| Cab-O-Sil silica | 0.5 |
| Butyl 077[1] | 1.0 |
| Trichlorofluoromethane | 44.5 |
| Dichlorodifluoromethane | 44.0 |

[1]Exxon Chemicals, isobutylene-isoprene copolymer gum, viscosity average molecular weight 425,000 (Flory)

The silica, oleic acid and diisopropyl sebacate were combined in a Waring Blendor and stirred at high speed for five minutes. The aluminum chlorhydroxide was added, and the dispersion was homogenized. The polymer gum was added to the trichlorofluoromethane at 0° C. in a closed container; and stirred for two hours to dissolve the gum. The gum solution was combined with the dispersion, packaged in a conventional aerosol container, and pressurized with dichlorodifluoromethane. The container was of the same dimensions as that of Example 8.

A two-second spray expelled 2.0 g of the composition and deposited 0.080 g of aluminum chlorhydroxide on the skin. The composition was effective in inhibiting perspiration for one day.

Having regard to the foregoing disclosure, the following is claimed as the inventive and patentable embodiments thereof:

1. An aerosol antiperspirant composition that is capable of being dispensed from aerosol containers with low mistiness and dustiness, comprising, in combination, an antiperspirant salt in an amount within the range from about 3 to about 30%; a liquid phase comprising a liquefied propellant in an amount within the range from about 15% to about 95%; a bulking agent in an amount within the range from about 0.1 to about 5%; and a synthetic polymer gum having a viscosity within the range from about 500,000 to about 100 million centistokes at 25° C., the synthetic polymer gum being in solution in the liquid phase in an amount within the range from about 0.05 to about 5% by weight of the composition to inhibit mistiness and dustiness.

2. An antiperspirant composition according to claim 1, in which the synthetic polymer gum is a silicone gum.

3. An antiperspirant composition according to claim 1, in which the synthetic polymer gum is an acrylic polymer.

4. An antiperspirant composition according to claim 1, in which the synthetic polymer gum is a hydrocarbon polymer.

5. An antiperspirant composition according to claim 1, comprising in addition a nonvolatile miscible organic liquid in an amount within the range from about 0.1 to about 30% by weight of the composition.

6. An antiperspirant composition according to claim 5, in which the organic liquid comprises in part an aliphatic, cycloaliphatic or aromatic carboxylic acid having from about nine to fifty carbon atoms, that enhances adhesion of the antiperspirant salt to the skin.

7. An antiperspirant composition according to claim 6, in which the carboxylic acid is an aliphatic acid.

8. An antiperspirant composition according to claim 6, in which the carboxylic acid is an aromatic acid.

9. An antiperspirant composition according to claim 6, in which the carboxylic acid is a cycloaliphatic acid.

10. An antiperspirant composition according to claim 5, in which the nonvolatile liquid is a carboxylic acid ester of an alcohol, the ester having from about twelve to about twenty-six carbon atoms.

11. An antiperspirant composition according to claim 10, in which the ester is isopropyl myristate.

12. An antiperspirant composition according to claim 1, in which the bulking agent comprises colloidal silica having a particle size below 10 microns in diameter.

13. An antiperspirant composition according to claim 1, in which the bulking agent comprises a hydrophobic clay having a particle size below 10 microns in diameter.

14. An antiperspirant composition according to claim 1, in which the antiperspirant salt is an aluminum salt.

15. An antiperspirant composition according to claim 14, in which the antiperspirant salt is aluminum chlorhydroxide.

16. An antiperspirant composition according to claim 14, in which the antiperspirant salt is aluminum chloride.

17. An antiperspirant composition according to claim 1, in which the antiperspirant salt is a zorconium salt.

18. An antiperspirant composition according to claim 1, in which the antiperspirant salt is a mixture of aluminum chlorhydroxide and zirconium chlorhydroxide.

19. An antiperspirant composition according to claim 1, in which the propellant is a hydrocarbon propellant.

20. An antiperspirant composition according to claim 1, in which the propellant is a halocarbon propellant.

21. An antiperspirant composition according to claim 1, in which the propellant is isobutane.

22. An antiperspirant composition according to claim 1, comprising a mixture of isobutane and another hydrocarbon or halocarbon propellant.

23. An aerosol antiperspirant composition that is highly concentrated with respect to the active antiperspirant, and capable of being dispensed from aerosol containers of the foam type at a low delivery rate in a propellant gas:liquid ratio within the range from about 10:1 to about 40:1 comprising, in combination, a liquid phase comprising a nonvolatile miscible organic liquid in an amount within the range from about 0.1 to about 30% by weight of the composition; a bulking agent in an amount within the range from about 0.1 to about 5%, and an antiperspirant salt in an amount within the range from about 8 to about 30%; a liquefied propellant having a vapor pressure of at least 2.4 atmospheres absolute at 21° C.; the liquefied propellant being in an amount of at least 0.15 mole per atmosphere absolute pressure at 21° C. per 100 g of composition to generate an expelled gas:liquid ratio within the range from about 10:1 to about 40:1; a carboxylic acid selected from the group consisting of aliphatic, cycloaliphatic and aromatic carboxylic acids having from about nine to about fifty carbon atoms comprising an amount within the range from about 0.1 to about 30% by weight of the composition and constituting part to all of the nonvolatile liquid, to improve adherence of the antiperspirant salt to the skin; and a synthetic polymer gum having a viscosity within the range from about 500,000 to about 100 million centistokes at 25° C., the synthetic polymer gum being in solution in the liquid phase in an amount within the range from about 0.1 to about 5% by weight of the composition to inhibit formation of stable aerosol dispersions in air of the liquid and solid phases when the composition is expelled from an aerosol container.

24. An antiperspirant composition according to claim 23, in which the synthetic polymer gum is a silicone gum.

25. An antiperspirant composition according to claim 23, in which the synthetic polymer gum is an acrylic polymer.

26. An antiperspirant composition according to claim 23, in which the synthetic polymer gum is a hydrocarbon polymer.

* * * * *

UNITED STATES PATENT AND TRADEMARK OFFICE
CERTIFICATE OF CORRECTION

PATENT NO. : 4,152,416

DATED : May 1, 1979

INVENTOR(S) : Joseph George Spitzer et al.

It is certified that error appears in the above-identified patent and that said Letters Patent are hereby corrected as shown below:

| | |
|---|---|
| Column 1, line 62 | "propellent" should be --propellant--. |
| Column 2, line 20 | "propellent" should be --propellant--. |
| Column 2, line 23 | "propellent" should be --propellant--. |
| Column 5, line 29 | "orgnic" should be --organic--. |
| Column 7, lines 4-5 | "dodecylsalicylic" should be --dodecylsalicyclic-- |
| Column 7, line 5 | "butoxybenzoic" should be --butoxylbenzoic--. |
| Column 7, line 5 | "oxtoxybenzoic" should be --octoxybenzoic--. |
| Column 7, line 35 | "acid" should be --acids--. |
| Column 10, line 54 | "aan" should be --an--. |
| Column 10, line 55 | Please delete "Ser. No. 670,913 filed March 26, 1976," and add --U.S. pat. No. 4,019,657 patented April 26, 1977,--. |
| Column 11, line 11 | "Ispropyl" should be --Isopropyl |
| Column 11, lines 32-33 | "chlordifluoromethane" should be --chlorodifluoromethane--. |
| Column 12, lines 4-5: | Please delete "Ser. No. 670,913 filed March 26, 1976" and add --U.S. pat. No. 4,019,657 patented April 26, 1977--. |

Page 1 of 2

UNITED STATES PATENT AND TRADEMARK OFFICE
CERTIFICATE OF CORRECTION

PATENT NO. : 4,152,416
DATED : May 1, 1979
INVENTOR(S) : Joseph George Spitzer et al.

It is certified that error appears in the above-identified patent and that said Letters Patent are hereby corrected as shown below:

Column 13, lines 20-21 : Please delete "Ser. No. 670,913 filed March 26, 1976" and add --U.S. pat. No. 4,019,657 patented April 26, 1977--.

Column 16, line 5 : "Zorconium" should be --Zirconium--.

Signed and Sealed this

Twenty-third Day of October 1979

[SEAL]

Attest:

RUTH C. MASON
Attesting Officer

LUTRELLE F. PARKER
Acting Commissioner of Patents and Trademarks